(12) United States Patent
Singh et al.

(10) Patent No.: US 9,163,257 B2
(45) Date of Patent: Oct. 20, 2015

(54) EXPRESSION VECTOR AND METHODS OF PRODUCING HIGH LEVELS OF PROTEINS

(75) Inventors: Arun K. Singh, Gujarat (IN); Ashish Goel, Gujarat (IN); Sanjeev K. Mendiratta, Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 1951 days.

(21) Appl. No.: 11/922,548

(22) PCT Filed: Jun. 19, 2006

(86) PCT No.: PCT/IN2006/000207
§ 371 (c)(1),
(2), (4) Date: Jan. 6, 2010

(87) PCT Pub. No.: WO2007/017903
PCT Pub. Date: Feb. 15, 2007

(65) Prior Publication Data
US 2011/0212518 A1    Sep. 1, 2011

(30) Foreign Application Priority Data
Jun. 20, 2005    (IN) ............................ 720/MUM/2005

(51) Int. Cl.
*C12N 15/00* (2006.01)
*C12N 15/85* (2006.01)
*C07K 14/715* (2006.01)

(52) U.S. Cl.
CPC ............ *C12N 15/85* (2013.01); *C07K 14/7151* (2013.01); *C07K 2319/30* (2013.01); *C12N 2710/10022* (2013.01); *C12N 2710/16122* (2013.01); *C12N 2830/42* (2013.01); *C12N 2840/60* (2013.01)

(58) Field of Classification Search
USPC ............................................. 435/325, 320.1
See application file for complete search history.

(56) References Cited

U.S. PATENT DOCUMENTS

| | | | | |
|---|---|---|---|---|
| 5,024,939 | A * | 6/1991 | Gorman ...................... | 435/69.1 |
| 6,001,973 | A * | 12/1999 | Strom et al. .................. | 530/351 |
| 6,063,598 | A * | 5/2000 | Enenkel et al. .............. | 435/69.1 |
| 6,613,319 | B2 * | 9/2003 | Leiden ......................... | 424/93.2 |
| 6,641,807 | B1 * | 11/2003 | Savino et al. ................ | 424/93.2 |
| 6,777,205 | B1 | 8/2004 | Carcagno et al. | |
| 6,924,415 | B2 * | 8/2005 | Olson et al. .................... | 800/18 |
| 7,294,481 | B1 * | 11/2007 | Fung ............................. | 435/69.1 |
| 2002/0076711 | A1 * | 6/2002 | Wolffe et al. ..................... | 435/6 |
| 2002/0103142 | A1 * | 8/2002 | Rolland et al. ................. | 514/44 |
| 2002/0122788 | A1 * | 9/2002 | Leiden .......................... | 424/93.1 |
| 2003/0157641 | A1 * | 8/2003 | Reff et al. ..................... | 435/69.1 |
| 2006/0223144 | A1 * | 10/2006 | Yang et al. .................... | 435/69.4 |

OTHER PUBLICATIONS

Mosley et al. (1989) The murine interleukin-4 receptor: molecular cloning and characterization of secreted and membrane bound forms. Cell 59(2): 335-348.*
Overell et al. (1991) Efficient gene transfer and expression in primary B lymphocytes. Journal of Immunological Methods 141: 53-62.*
Yew et al. (1997) Optimization of plasmid vectors for high-level expression in lung epithelial cells. Human Gene Therapy 8: 575-584.*
Hanauer et al. (2000) Human cytomegalovirus IE1 promoter/enhancer drives variable gene expression in all fiber types in transgenic mouse skeletal muscle. BMC Genetics 1:1 (pp. 1-7).*
Overell (J. Immunological Methods, 1991, 141: 53-62).*
Mosley (Cell, 1989, 59(2): 335-348).*
Yim, Su-Bin, et al. "Construction and Production of Concatameric Human TNF Receptor-Immunoglobulin Fusion Proteins." *Journal of Microbiology and Biotechnology* (2004) vol. 14, No. 1, pp. 81-89.
Thiel, Karl A. "Biomanufacturing, from bust to boom . . . to bubble?" *Nature Biotechnology* (2004) vol. 22, No. 11, pp. 1365-1372.
Wong, G. G., et al. "Human GM-CSF: Molecular Cloning of the Complementary DNA and Purification of the Natural and Recombinant Proteins." *Science* (1985) vol. 228, No. 4701, pp. 810-815.

* cited by examiner

*Primary Examiner* — Michael Wilson
(74) *Attorney, Agent, or Firm* — Ladas & Parry LLP

(57) ABSTRACT

A process for high expression of protein of interest using an expression vector. The process comprises at least the following regulatory elements: a) a CMV promoter, or its functional variants, b) an intron, c) TPL or its functional variants, d) VA genes or functional variants, and e) a bovine growth hormone polyadenylation sequence or functional variants.

19 Claims, 3 Drawing Sheets

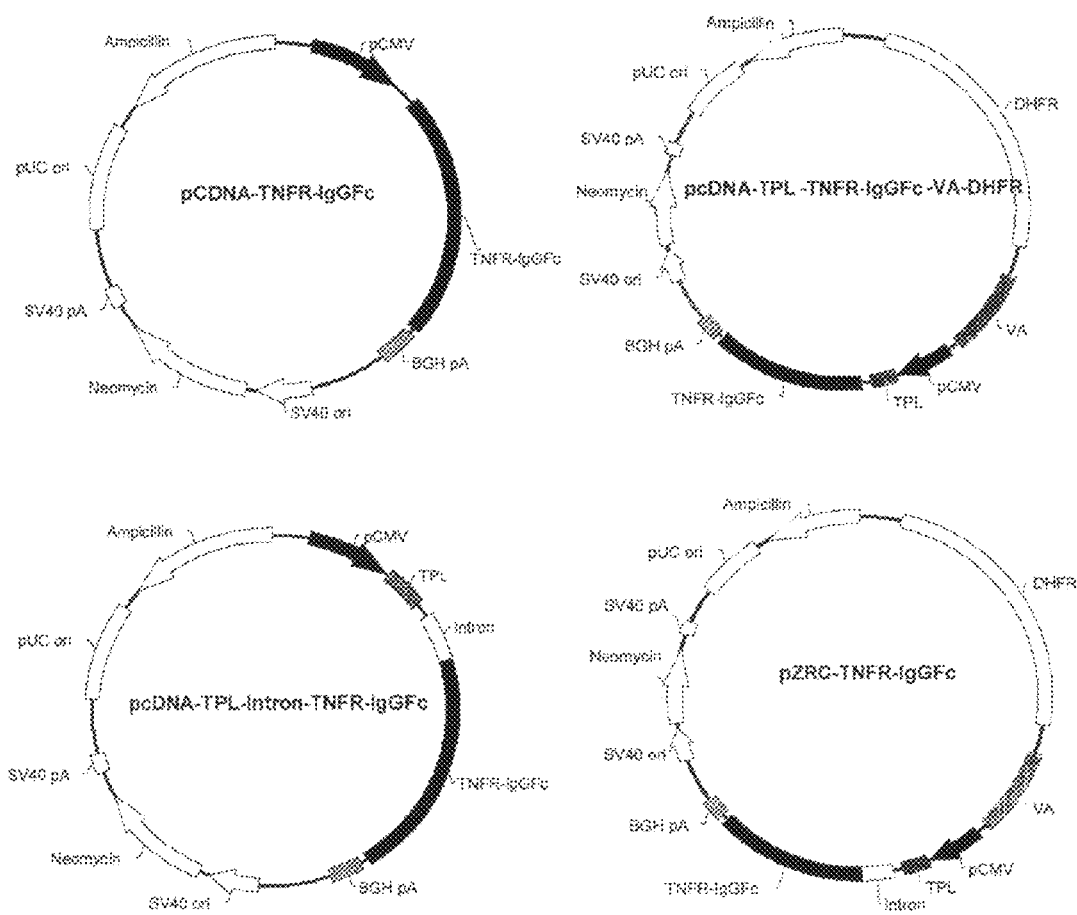
Figure 1. TNFR-IgGFc Expression Vectors

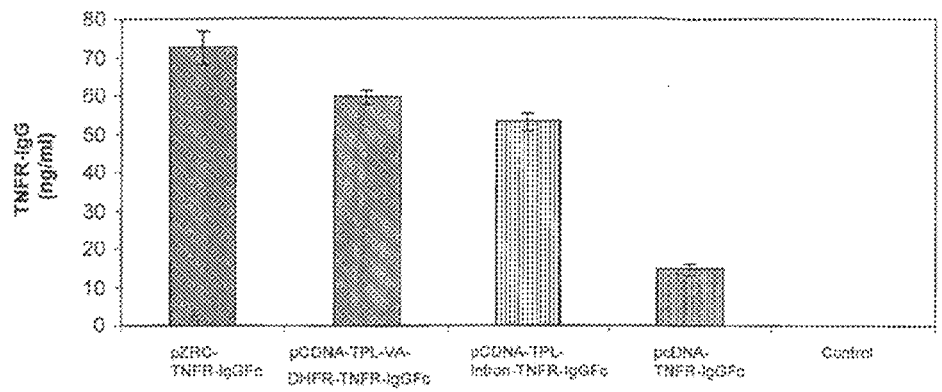
Figure 2. Transient transfection of Cos-1 Cells with TNFR-IgGFc expression vectors
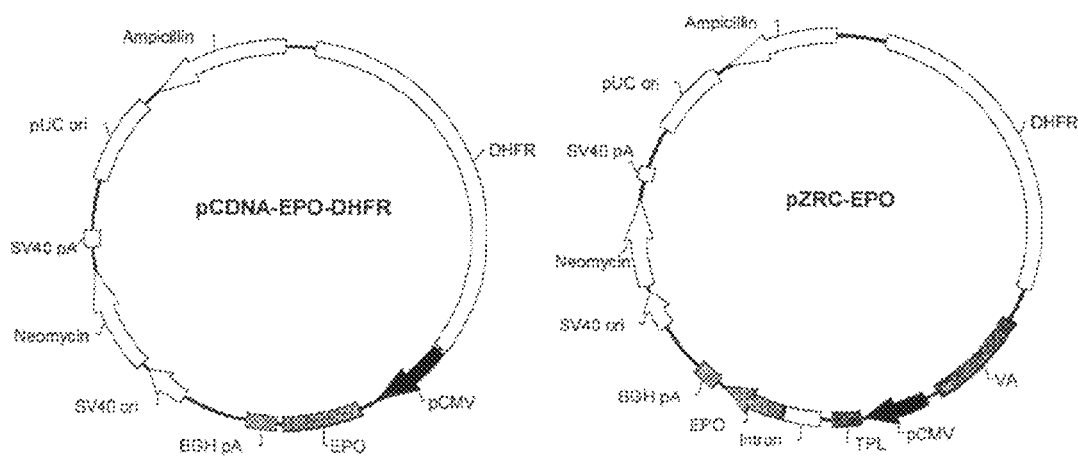
Figure 3. EPO Expression Vectors

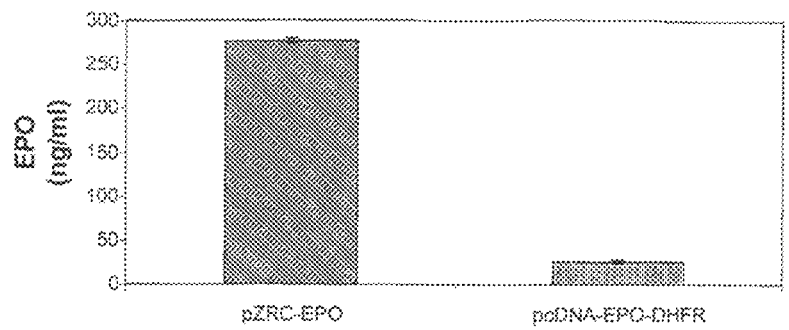
Figure 4. Transient transfection of Cos-1 cells with EPO expression vectors
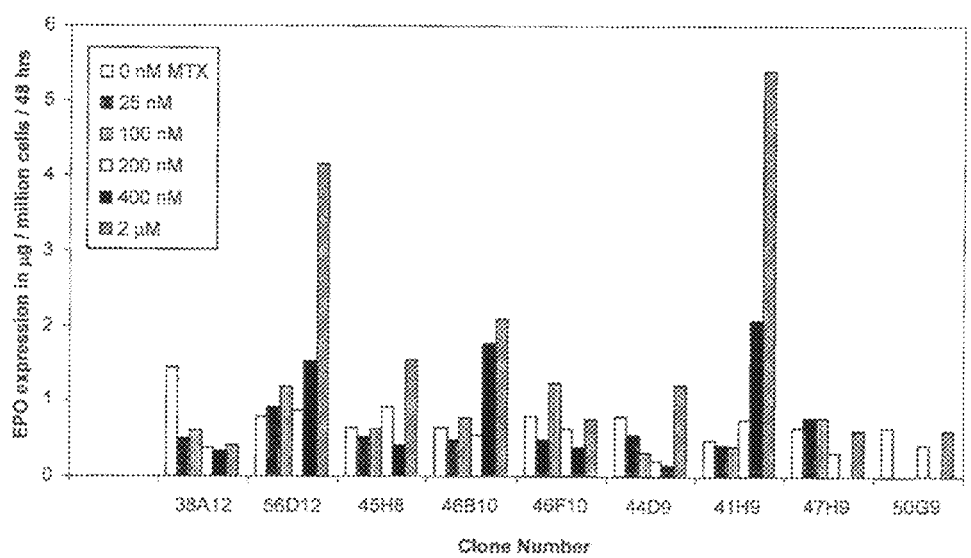
Fig 5 Effect of increasing pressure of MTX on EPO expression from selected high producing clones of CHO-DHFR- cells stably transfected with pZRC-EPO.

SEQUENCE LISTING

```
<160> NUMBER OF SEQ ID NOS: 5

<210> SEQ ID NO 1
<211> LENGTH: 291
<212> TYPE: DNA
<213> ORGANISM: Artificial sequence
<220> FEATURE:
<223> OTHER INFORMATION: This sequence was artificially  generated as a
      hybrid of an adenovirus gene component and a mouse gene component
<220> FEATURE:
<221> NAME/KEY: misc_feature
<222> LOCATION: (5)..(5)
<223> OTHER INFORMATION: deoxy ribose
<220> FEATURE:
<221> NAME/KEY: misc_feature
<222> LOCATION: (216)..(218)
<223> OTHER INFORMATION: n is a, c, g, or t
<220> FEATURE:
<221> NAME/KEY: exon
<222> LOCATION: (218)..(219)
<223> OTHER INFORMATION: deoxy ribose

<400> SEQUENCE: 1
ggaattaatt cgctgtctgc gagggccagc tgttggggtg agtactccct ctcaaaagcg      60
ggcatgactt ctgcgctaag attgtcagtt tccaaaaacg ggaggatttg atattcacct     120
ggcccgcggt gatgcctttg agggtggccg cgtccatctg gtcagaaaag acaatctttt     180
tgttgtcaag cttgaggtgt ggcaggcttg agatcnn nt ggccatacac ttgagtgaca     239
atgacatcca ctttgccttt ctctccacag gtgtccactc ccaggtccaa ct            291

<210> SEQ ID NO 2
<211> LENGTH: 1470
<212> TYPE: DNA
<213> ORGANISM: homo sapiens

<400> SEQUENCE: 2
atggcgcccg tcgccgtctg ggccgcgctg gccgtcggac tggagctctg ggctgcggcg      60
cacgccttgc ccgcccaggt ggcatttaca ccctacgccc cggagcccgg gagcacatgc     120
cggctcagag aatactatga ccagacagct cagatgtgct gcagcaaatg ctcgccgggc     180
caacatgcaa aagtcttctg taccaagacc tcggacaccg tgtgtgactc ctgtgaggac     240
agcacataca cccagctctg gaactgggtt cccgagtgct tgagctgtgg ctcccgctgt     300
agctctgacc aggtggaaac tcaagcctgc actcgggaac agaaccgcat ctgcacctgc     360
aggcccggct ggtactgcgc gctgagcaag caggagggt gccggctgtg cgcgccgctg     420
```

```
cgcaagtgcc gcccgggctt cggcgtggcc agaccaggaa ctgaaacatc agacgtggtg    480
tgcaagccct gtgccccggg gacgttctcc aacacgactt catccacgga tatttgcagg    540
ccccaccaga tctgtaacgt ggtggccatc cctgggaatg caagcatgga tgcagtctgc    600
acgtccacgt cccccacccg gagtatggcc caggggcag tacacttacc ccagccagtg     660
tccacacgat cccaacacac gcagccaact ccagaaccca gcactgctcc aagcacctcc    720
ttcctgctcc caatgggccc cagcccccca gctgaaggga gcactggcga cgagcccaaa    780
tcttgtgaca aaactcacac atgcccaccg tgcccagcac ctgaactcct ggggggaccg    840
tcagtcttcc tcttcccccc aaaacccaag gacaccctca tgatctcccg gacccctgag    900
gtcacatgcg tggtggtgga cgtgagccac gaagaccctg aggtcaagtt caactggtac    960
gtggacggcg tggaggtgca taatgccaag acaaagccgc gggaggagca gtacaacagc   1020
acgtaccgtg tggtcagcgt cctcaccgtc ctgcaccagg actggctgaa tggcaaggag   1080
tacaagtgca aggtctccaa caaagccctc ccagccccca tcgagaaaac catctccaaa   1140
gccaaagggc agccccgaga accacaggtg tacaccctgc ccccatcccg ggaggagatg   1200
accaagaacc aggtcagcct gacctgcctg gtcaaaggct tctatcccag cgacatcgcc   1260
gtggagtggg agagcaatgg gcagccggag aacaactaca agaccacgcc tcccgtgctg   1320
gactccgacg gctccttctt cctctatagc aagctcaccg tggacaagag caggtggcag   1380
caggggaacg tcttctcatg ctccgtgatg catgaggctc tgcacaacca ctacacgcag   1440
aagagcctct ccctgtcccc gggtaaatga                                    1470

<210> SEQ ID NO 3
<211> LENGTH: 582
<212> TYPE: DNA
<213> ORGANISM: homo sapiens

<400> SEQUENCE: 3
atgggggtgc acgaatgtcc tgcctggctg tggcttctcc tgtccctgct gtcgctccct     60
ctgggcctcc cagtcctggg cgccccacca cgcctcatct gtgacagccg agtcctggag    120
aggtacctct tggaggccaa ggaggccgag aatatcacga cgggctgtgc tgaacactgc    180
agcttgaatg agaatatcac tgtcccagac accaaagtta atttctatgc ctggaagagg    240
atggaggtcg ggcagcaggc cgtagaagtc tggcagggcc tggccctgct gtcggaagct    300
gtcctgcggg gccaggccct gttggtcaac tcttcccagc cgtgggagcc cctgcagctg    360
catgtggata aagccgtcag tggccttcgc agcctcacca ctctgcttcg ggctctggga    420
gcccagaagg aagccatctc ccctccagat gcggcctcag ctgctccact ccgaacaatc    480
actgctgaca ctttccgcaa actcttccga gtctactcca atttcctccg gggaaagctg    540
aagctgtaca cagggggaggc ctgcaggaca ggggacagat ga                      582

<210> SEQ ID NO 4
<211> LENGTH: 373
<212> TYPE: DNA
<213> ORGANISM: Artificial Sequence
<220> FEATURE:
<223> OTHER INFORMATION: This sequence was generated from adenovirus GI:
      209811

<400> SEQUENCE: 4
cttccgcatc gctgtctgcg agggccagct gttggggtga gtactccctc tcaaaagcgg     60
gcatgacttc tgcgctaaga ttgtcagttt ccaaaaacga ggaggatttg atattcactg    120
```

```
gcccgcggtg atgcctttga gggtggccgc gtccatctgg tcagaaaaga caatcttttt    180
gttgtcaagc ttccttgatg atgtcatact tatcctgtcc cttttttttc cacagctcgc    240
ggttgaggac aaactcttcg cggtctttcc agtactcttg gatcggaaac ccgtcggcct    300
ccgaacggta ctccgccacc gagggacctg agcgagtccg catcgaccgg atcggaaaac    360
ctctcgaggt acc                                                       373

<210> SEQ ID NO 5
<211> LENGTH: 417
<212> TYPE: DNA
<213> ORGANISM: Artificial Sequence
<220> FEATURE:
<223> OTHER INFORMATION: This sequence was generated from adenovirus GI:
      209811

<400> SEQUENCE: 5
agcgggcact cttccgtggt ctggtggata aattcgcaag ggtatcatgg cggacgaccg     60
gggttcgaac cccggatccg gccgtccgcc gtgatccatg cggttaccgc ccgcgtgtcg    120
aacccaggtg tgcgacgtca gacaacgggg gagcgctcct tttggcttcc ttccaggcgc    180
ggcggctgct gcgctagctt ttttggccac tggccgcgcg cggcgtaagc ggttaggctg    240
gaaagcgaaa gcattaagtg gctcgctccc tgtagccgga gggttatttt ccaagggttg    300
agtcgcagga cccccggttc gagtctcggg ccggccggac tgcggcgaac gggggtttgc    360
ctccccgtca tgcaagaccc cgcttgcaaa ttcctccgga aacagggacg agcccct      417
```

EXPRESSION VECTOR AND METHODS OF PRODUCING HIGH LEVELS OF PROTEINS

FIELD OF INVENTION

The present invention relates to novel expression vectors for the production of high levels of recombinant proteins in mammalian cells and process of producing the proteins of interest by using the same. These expression vectors give 80-100% higher expression of a recombinant protein EPO than some of the best vectors reported in the literature.

BACKGROUND OF THE INVENTION

According to IMS health, the biopharmaceuticals' share of the total pharmaceutical market is forecast to grow from 6 percent in 1999 to 14 percent ($90 billion) in 2009. This increased demand of biologicals is primarily due to their generally highly specific target of action which results in significantly reduced and well-defined risk of toxicity compared to small molecule based drugs. Further, by employing recombinant techniques to produce these biologicals in contrast with older techniques of purifying them from tissue extracts or body fluids, products of very high purity, and well-defined safety and physicochemical characteristics, can be easily produced. Despite having all these patient-friendly qualities, most recombinant biologics remain inaccessible to most people in the world because they continue to remain prohibitively expensive. Therefore, life saving drugs like erythropoietin, drugs like etanercept that significantly improve quality of life, and many anti-cancer drugs like rituximab, trastuzumab and all other monoclonal antibodies etc., are afforded only by a very small percentage of people while a vast majority of sick people around the world cannot use them enough. There is therefore an urgent need to bring down the cost of these drugs. A large component of this high cost is that associated with manufacturing them. This invention provides a solution to this problem by providing expression vectors than can give high expression of protein in mammalian host cells transfected with them.

In recent years, recombinant DNA technology has advanced to a stage where, in general, it is readily possible to obtain a desired gene encoding a desired protein product, also called a biological when the protein is subsequently used as a therapeutic. Once the gene is obtained, a variety of hosts can be employed for its expression by first cloning the gene into any one of a number of available host-specific expression vectors, followed by introducing the gene-carrying vector into the specific host by using a variety of transformation or transfection methods. In order to get protein production from these gene-transformed host cells a variety of conditions of fermentation are also available. Selection of the host and the subsequent interdependent selections such as that of expression vectors, transformation and transfection techniques and fermentation methodologies, depend upon many factors such as, characteristics of the protein to be produced, ultimate use of the protein, amount of the protein required, purification methods available, overall cost and available technology etc. For example, relevant to the interest of this invention where the recombinant protein produced is meant for therapeutic applications, the primary, secondary and tertiary structure of the protein, degree and quality of its glycosylation, purity of the final product, the amount of protein produced, cost at which the drug can be sold, all contribute to the above process of selecting the expression host and making other interdependent selections.

One possible solution for addressing the above described problem of high cost of production of biologicals is to express them in bacterial host cells, such as *E. coli* [Marino, M. H., *BioPharm*, 2:18-33 (1989); Georgiou G., *Protein engineering: Principles and practice*, Wiley Liss, New York 101-127 (1996); Gold, L. *Methods Enzymol*, 185:11-14 (1990); Hodgson, J., *Bio/Technology*, 11:887-893 (1993); Nicaud et al, *J. Biotechnol.* 3:255-270 (1986); Olins, P. O., and S. C. Lee., *Curr. Opin. Biotechnol.* 4:520-525 (1993); Shatzman, A. R., *Curr. Opin. Biotechnol*, 6:491-493 (1995)]. A commonly used bacterial host, *Escherichia coli*, is an important host organism for the production of recombinant proteins and is widely used in industrial production. Its many advantages include easy cultivation, low cost, and high production potential [Shuhua Tan et al, *Protein Expression and Purification*, 25:430-436 (2002); Cornelia Rossmann et al, *Protein expression and Purification* 7:335-342 (1996)]. However, bacterial hosts are generally not ideal for the production of biologicals because they do not have the necessary machinery to glycosylate proteins [Old R W, and Primrose S. B., *Principles of Gene Manipulations, An introduction to genetic Engineering*, Blackwell science, United Kingdom. (1994)], and most mammalian therapeutic proteins are not fully functional without proper glycosylation. Additionally, the lack of a secretion mechanism for the efficient release of protein into the culture medium, the limited ability to facilitate extensive disulfide bond formation, improper folding, degradation of the protein by host cell proteases, significant differences in codon usage, other modifications such as glycations etc., together make bacterial systems much less attractive than mammalian systems [Fuh, G. et al., *J. Biol. Chem.*, 265:3111-3115 (1990); Liang et al., *Biochem. J.*, 229:429-439 (1985); Sarmientos et al., *Bio/Technology*, 7:495-501 (1989); Savvas C. Makrides, *Microbiological Reviews*, September 1996. 512-538; N. Jenkins and E. M. Curling, *Enzyme Microb. Technol.*, 16:354-364 (1994)]. Therefore, it is not usually possible to express therapeutic proteins in bacteria and most biologicals utilize eukaryotic host cells for expression even though this means higher cost of production, due to lower expression levels of recombinant protein, more stringent requirements for culturing, slower growth rates etc (Cornelia Rossmann, *Protein Expression and Purification*, 7:335-342 (1996); Geoff T. Yarranton, *Current Opinion in Biotechnology*, 1:133-140 (1990)].

Since mammalian host systems are highly advantageous in therapeutic protein production, it is highly important to address this issue of high cost of production associated with them. Since cost of manufacturing can be brought down by increasing productivity, a considerable effort has been expended on increasing the amount of product which can be produced by these host cells. The factors which normally control the amount of product produced by a host cell, include factors which are external to the cell such as the culture conditions, and those which are internal to the cells majority of which include factors that regulate the efficiency and quality of transcription [Foecking and Hofstetter, *Gene*, 45:101-105 (1986); Kaufman et al, *Journal of molecular Biology*, 159:601-621 (1985); Wurm et al, *PNAS*, 1983:5414-5418 (1986); Reiser and Hauser, *Drug Research*, 37:482-485 (1987); Zettimeissl et al, *Biotechnology*, 5:720-725 (1987)] and translation [(R. Grabherr and K. Bayer, *Food Technol. Biotechnol.* 39 (4) 265-269 (2001); Randal J. Kaufman et al. *Molecular Biotechnology*, 16 (2), 151-160, (2000); Juraj Hlavaty et al., *Virology* 341, 1-11, (2005); C. M. Stenstrom et al., *Gene*. 273(2), 259-65, (2001). M. Ibba and D. Soil, *Science*, 186, 1893, (1999)] and are predominantly dependent upon the design of the expression vector itself. Even though, literature reports many efforts to increase host cell productivity by improving the culturing conditions [Palermo D. P. et al., *Journal of Biotechnology*, 19:35-48 (1991); Birch and Froud, *Biologicals*, 22:127-133 (1994); Osman et al, *Biotechnology and Bioengineering*, 77:398-407 (2003); Dezengotita et al, *Biotechnology and Bioengineering*, 77:369-380 (2002); Schmelzer & Miller, *Biotechnology Prog.*, 18:346-353 (2002); Dezengotita et al., *Biotechnology and Bioengineering*, 78:741-752 (2002); and Sun et al, *Biotechnology Prog.*, 20:576-589 (2004)], improvements in these external factors can increase the expression to a limited extent only and are commercially ineffective unless the expression vector has been optimized first to get an ideal basal level of expression.

A vast number of studies have been reported in the prior art that address the internal factors for improving gene expression. The internal factors described below are also known as regulatory elements that regulate gene expression in many ways. It is well known in the prior art that for a gene of interest to get expressed from an expression vector it has to be placed under the control of appropriate 5' and 3' flanking sequences which allow the gene to be transcribed into mRNA and then accurately translated into protein. Many important 5' and 3' flanking sequences, such as TATA boxes [Boshart, M. et al., *Cell*, 41:521-530 (1985); Browning, K. S. et al. *J. Biol. Chem.*, 263:9630-9634 (1998); Dorsch-Hasler, K. et al., *PNAS*, 82:8325-8329 (1985)], promoters such as viral promoters like the CMV immediate early, promoter, SV40 early or late promoters, the adenovirus major late promoter [Luigi R., *Gene*, 168:195-198 (1996); Pizzorno, M. C. et al., *J. Virol.*, 62:1167-1179 (1988); Okayama and Berg, *Mol. Cell. Biol.*, 2:161-171 (1982); Wong et al., *Science*, 228:810-815 (1985); Foecking and Hofsteffer, *Gene*, 45:101-105 (1986)], and mammalian promoters such as the mouse metallothionin promoter, the chicken β-actin promoter [Nicole Israel et al., *Gene*, 51:197-204 (1987); Karin, M. and Richards, *Nature*, 299:797-802 (1982); Miyazaki et al., *Proc. Natl. Acad. Sci. USA*, 83:9537-9541 (1986)], enhancers such as CMV immediate early enhancer [Cockett, M. I. et al., *Nucleic Acids Research*, 19:319-325 (1996)], translation start and stop codons [Lehninger et al, Principles of Biochemistry—3$^{rd}$ edition, Worth Publishers, Chapter 27, p1025], and polyadenylation sites such as bovine growth hormone (BGH) and SV40 polyadenylation sites [Carswell, S. and Alwine, J. C, *Mol. Cell. Biol.* 9:4248-4258 (1989)] have been reported. Introns are another internal factor that normally form an integral part of eukaryotic genes as intervening sequences between exons and that are precisely deleted from the primary transcript by a process known as RNA splicing to form mature mRNA. RNA splicing has been widely demonstrated to be responsible for mRNA stability [Buchman et al, *Mol. Cell. Biol.* 8:4395-404 (1988); Peterson et al, *Proc. Natl. Acad. Sci. USA*, 83:8883-87 (1986)], and regulation of gene expression [Brinster et al, *Proc. Natl. Acad. Sci. USA*, 85:836-40 (1988); Dynan, W. S. and Tjian, R., *Nature*, 316:774-778 (1985)]. Synthetic chimeric introns have also been developed such as the one reported by Huang et al that consists of 5' donor site of the adenovirus major late transcript and the 3' splice site of an mouse immunoglobulin [Huang et al, *Nucleic Acids Res.*, 18:937-47 (1990)]. Such chimeric introns support heterologous gene expression better than other commonly used introns [Huang et al, *Nucleic Acids Res.*, 18:937-47 (1990); Ted Choi et al, *Molecular and Cellular Biology*, 11 (6): 3070-3074 (1991)]

A commonly utilized source for highly efficient internal factors is viruses. Viruses are well known to be the most efficient parasites in nature that use their own internal factors to manipulate host and viral gene expression in favor of their propagation and survival. These have also been studied extensively for their role in the design of expression vectors to ultimately improve protein production. Some of the most efficient promoters known in the art of molecular biology are derived from viruses [Luigi R., *Gene*, 168:195-198 (1996); Pizzorno, M. C. et al., *J. Virol.*, 62:1167-1179 (1988); Okayama and Berg, *Mol. Cell. Biol.*, 2:161-171 (1982); Wong et al., *Science*, 228:810-815 (1985); Foecking and Hofsteffer, *Gene*, 45:01-105 (1986)]. Many viruses have been studied extensively at the genetic level and individual sequences have been identified which can alter the nuclear and cytoplasmic metabolism of mRNA in the host cells. Adenovirus tripartite leader element (TPL) (GI: 209811) [Akusjarvi G. et al, *J Mol. Biol.*, 134(1):143-58 (1979)] is one of such elements known to enhance the translation of even a non-viral RNA in the virus-infected cells when directly appended to it [Berkner K. L. et al, *Nucleic Acids Res.*, 13(3):841-57 (1985)]. All the mRNAs encoded by adenovirus major late transcription unit share this common 5' non-coding region. This element can reduce the nuclear half-life of the transcripts [Huang et al, *J. Virol.*, 2(1):225-35 (1998)]. This element is also known to enhance the translation of the mRNAs [Kaufman R. J. et al, *Proc Natl Acad Sci USA.*, 82(3):689-93 (1985)]. Another element is the Adenoviral Virus Associated RNA genes I & II (GI: 209811) or its functional variants. The VA RNA genes I & II (VA genes) have been shown to increase the translation efficiency of the gene containing the TPL sequence [Kaufman R. J. et al, *Proc Natl Acad Sci USA.*, 82(3):689-93 (1985)]. The VA RNA I gene is involved in the dephosphorylation of EIF2a and thus increases the protein synthesis rates [O'Malley et al, *Cell*, 44:391-400 (1986); Thimmapayya B., et al, *Cell*, 31:543-551 (1982)].

Another commonly utilized internal factor is the gene copy number which is a favored approach for increasing gene expression [Kaufman and Sharp, *Journal of molecular Biology*, 159:601-602 (1982); Pendse G. J. et al, *Biotechnology and Bioengineering*, 40:119-129 (1992); Schimke, R. T. (Ed.), *Gene Amplification*. Cold Spring Harbor Laboratory, Cold Spring Harbor, N.Y., 1982]. The most common method used to increase gene copy number is to select cells for gene amplification. In this approach—for instance as described in EP0045809 or U.S. Pat. No. 4,634,665—a host cell is transformed with a pair of genes. The first gene in the pair is encoding a desired protein and the second gene is encoding a selectable marker, e.g., dihydrofolate reductase (DHFR) [Alt, F. W. et al., *J. Biol. Chem.*, 253:1337-1370 (1978)]. These two genes are either present on a single expression vector or on two separate expression vectors. After transfecting cells with this pair of genes, they are cultured in increasing concentrations of a toxic agent, such as methotrexate in the case of the method utilizing DHFR gene as a selection marker, the effect of which is nullified by the product of the selectable marker gene. It has been found that those cell lines, which survive in the higher concentrations of the toxic agent, have an increased copy number of both the selectable marker gene and the desired product gene. The selected host cell that has an amplified number of relevant gene copies can now produce a larger amount of the desired protein than the original cell line. A similar strategy for gene amplification has been utilized using other selection markers such as, adenosine deaminase (ADA), ornithine decarboxylase (ODC), asparagine synthetase (AS) [Chiang, T. and McConlogue, *Mol. Cell. Biol.* 764-769 (1988); Cartier, M. et al., *Mol. Biol.*, 7:1623-1628 (1987); Germann, U. A. et al., *J. Biol. Chem.* 264:7418-7424 (1989); Mkeille Cartier and Clifford P. Stanners, *Gene*, 95:223-230 (1990); Wood C. R. et al., *J Immunol*, 145:3011-3016 (1990); Kellems R. E. et al., In *Genetics and Molecular*

*Biology of Industrial Microorganisms*, American Society for Microbiology, Washington, 215-225 (1989)], and glutamine synthetase (GS) [Catherine W-H. et al., *J. Biol. Chem.*, 276: 43, 39577-39585 (2001); Bebbington, et al., *Biotechnology*, 10:169-175 (1992); Bebbington, C. R., *Monoclonal antibodies: the next generation*, Zola, H., (ed). Bios Scientific, Oxford, 65-181 (1995); Wilson, R. H., In "*Gene Amplification in Mammalian Cells*" ed Kellens, R. E., Marcel Dekker Inc., New York, 301-311 (1993)] also.

These above described regulatory elements or internal factors are independently, generally incapable of giving gene expression and must be used in combinations. However, while the elements themselves have been well understood the efficiency of their combinations is not absolutely predictable for high expression. Some combinations give very poor expression in comparison with others. For example, king et al using an expression vector consisting of a combination of SR α promoter, AMV RNA leader sequence and DHFR could get an erythropoietin (EPO) expression of only 45 IU/ml (equivalent to 0.346 µg/ml) [Jang H P et al, *Biotechnol. Appl. Biochem*, 32:167-172, (2000)], while U.S. Pat. No. 5,955,422, reports levels of EPO of 750 to 1470 U/million cells/48 Hrs (or 375 to 735 U/million cells/24 Hrs) using an expression vector consisting of another combination of elements namely, SV40 promoter and poly A sequence, and DHFR. Still another expression vector reported in U.S. Pat. No. 5,888, 774, and consisting of a combination of EF1 promoter and apoB SAR elements reports an expression of 1500 to 1700 IU of EPO/million cells/24 Hrs. For other recombinant proteins such as TNFR-IgGFc (Enbrel) an expression vector containing a combination of CMV promoter, TPL, VA I & II, and DHFR has been reported [U.S. Pat. No. 5,605,690, Cindy A Jacobs and Craig A Smith].

Despite all the advances described above, the high cost of manufacturing of recombinant biologics, especially those utilizing mammalian expression systems, still remains a major concern. Therefore, even though prior art reports a large number of methods to increase protein expression by modulating the expression vector, it is still desirable to develop novel expression vectors for further increasing the productivity of eukaryotic host cells. Surprisingly, despite the tremendous amount of knowledge generated in this area over the last two decades even today a person skilled in the art cannot simply pick and choose a combination of internal factors or regulatory elements to design an expression vector that would give guaranteed high expression. A particular element when added to a combination may not provide any significant additive or synergistic effect to the expression potential of the vector. Therefore the process of developing a novel expression vector that would give high level of protein expression still requires empirically testing many possibilities. We have invented a novel expression vector that upon stable transfection in CHO-DHFR⁻ cells gives an expression of 11,830 IU/ml (91 µg/ml) in a 168 hrs culture, which is equivalent to 2366 to 3549 IU/$10^6$ cells/24 Hrs or 18.2 to 27.3 µg/$10^6$ cells/24 Hrs. Surprisingly, this level of expression for EPO is 80-100% higher than some of the best vectors reported in the literature. This novel expression vector will significantly bring down the cost of production of EPO and other recombinant biologicals.

SUMMARY OF THE INVENTION

The present invention solves the problem described earlier in the background by providing novel expression vectors for the highly improved production of recombinant proteins in mammalian cells. It also provides a method for making such vectors and a method of using such vectors for obtaining the high level expression of proteins.

Thus, one of the primary objects of the present invention is to provide an improved process for obtaining high expression levels of proteins of interest by the use of a novel vector as described herein.

The following sequences have been employed in the present invention:

```
Type: DNA
Length: 288
Sequence Name: Hybrid Intron
Source Organism: Hybrid of an adenovirus gene component
and a mouse gene component
Sequence:
                                                            SEQ ID NO. 1
GGAATTAATT CGCTGTCTGC GAGGGCCAGC TGTTGGGGTG AGTACTCCCT CTCAAAAGCG  60

GGCATGACTT CTGCGCTAAG ATTGTCAGTT TCCAAAAACG GGAGGATTTG ATATTCACCT 120

GGCCCGCGGT GATGCCTTTG AGGGTGGCCG CGTCCATCTG GTCAGAAAAG ACAATCTTTT 180

TGTTGTCAAG CTTGAGGTGT GGCAGGCTTG AGATCTGGCC ATACACTTGA GTGACAATGA 240

CATCCACTTT GCCTTTCTCT CCACAGGTGT CCACTCCCAG GTCCAACT           288

Type: DNA
Length: 1470
Sequence Name: TNFR-IgGFc
Source: Human placental RNA
                                                            SEQ ID NO. 2
ATGGCGCCCGTCGCCGTCTGGGCCGCGCTGGCCGTCGGACTGGAGCTCTGGGCTGCGGCGCACGCCTTGCCCGCC   75

CAGGTGGCATTTACACCCTACGCCCCGGAGCCCGGGAGCACATGCCGGCTCAGAGAATACTATGACCAGACAGCT  150

CAGATGTGCTGCAGCAAATGCTCGCCGGGCCAACATGCAAAAGTCTTCTGTACCAAGACCTCGGACACCGTGTGT  225

GACTCCTGTGAGGACAGCACATACACCCAGCTCTGGAACTGGGTTCCCGAGTGCTTGAGCTGTGGCTCCCGCTGT  300

AGCTCTGACCAGGTGGAAACTCAAGCCTGCACTCGGGAACAGAACCGCATCTGCACCTGCAGGCCCGGCTGGTAC  375

TGCGCGCTGAGCAAGCAGGAGGGGTGCCGGCTGTGCGCGCCGCTGCGCAAGTGCCGCCCGGGCTTCGGCGTGGCC  450
```

```
AGACCAGGAACTGAAACATCAGACGTGGTGTGCAAGCCCTGTGCCCCGGGGACGTTCTCCAACACGACTTCATCC    525

ACGGATATTTGCAGGCCCCACCAGATCTGTAACGTGGTGGCCATCCCTGGGAATGCAAGCATGGATGCAGTCTGC    600

ACGTCCACGTCCCCCACCCGGAGTATGGCCCCAGGGGCAGTACACTTACCCCAGCCAGTGTCCACACGATCCCAA    675

CACACGCAGCCAACTCCAGAACCCAGCACTGCTCCAAGCACCTCCTTCCTGCTCCCAATGGCCCCAGCCCCCCA    750

GCTGAAGGGAGCACTGGCGACGAGCCCAAATCTTGTGACAAAACTCACACATGCCCACCGTGCCCAGCACCTGAA   825

CTCCTGGGGGGACCGTCAGTCTTCCTCTTCCCCCCAAAACCCAAGGACACCCTCATGATCTCCCGGACCCCTGAG   900

GTCACATGCGTGGTGGTGGACGTGAGCCACGAAGACCCTGAGGTCAAGTTCAACTGGTACGTGGACGGCGTGGAG   975

GTGCATAATGCCAAGACAAAGCCGCGGGAGGAGCAGTACAACAGCACGTACCGTGTGGTCAGCGTCCTCACCGTC  1050

CTGCACCAGGACTGGCTGAATGGCAAGGAGTACAAGTGCAAGGTCTCCAACAAAGCCCTCCCAGCCCCCATCGAG  1125

AAAACCATCTCCAAAGCCAAAGGGCAGCCCCGAGAACCACAGGTGTACACCCTGCCCCCATCCCGGGAGGAGATG  1200

ACCAAGAACCAGGTCAGCCTGACCTGCCTGGTCAAAGGCTTCTATCCCAGCGACATCGCCGTGGAGTGGGAGAGC  1275

AATGGGCAGCCGGAGAACAACTACAAGACCACGCCTCCCGTGCTGGACTCCGACGGCTCCTTCTTCCTCTATAGC  1350

AAGCTCACCGTGGACAAGAGCAGGTGGCAGCAGGGGAACGTCTTCTCATGCTCCGTGATGCATGAGGCTCTGCAC  1425

AACCACTACACGCAGAAGAGCCTCTCCCTGTCCCCGGGTAAATGA                                 1470

Type: DNA
Length: 583
Sequence Name: Human Erythropoietin cDNA
Source: Human kidney RNA
                                                           SEQ ID NO. 3
ATGGGGGTGCACGAATGTCCTGCCTGGCTGTGGCTTCTCCTGTCCCTGCTGTCGCTCCCT    60

CTGGGCCTCCCAGTCCTGGGCGCCCCACCACGCCTCATCTGTGACAGCCGAGTCCTGGAG   120

AGGTACCTCTTGGAGGCCAAGGAGGCCGAGAATATCACGACGGGCTGTGCTGAACACTGC   180

AGCTTGAATGAGAATATCACTGTCCCAGACACCAAAGTTAATTTCTATGCCTGGAAGAGG   240

ATGGAGGTCGGGCAGCAGGCCGTAGAAGTCTGGCAGGGCCTGGCCCTGCTGTCGGAAGCT   300

GTCCTGCGGGGCCAGGCCCTGTTGGTCAACTCTTCCCAGCCGTGGGAGCCCCTGCAGCTG   360

CATGTGGATAAAGCCGTCAGTGGCCTTCGCAGCCTCACCACTCTGCTTCGGGCTCTGGGA   420

GCCCAGAAGGAAGCCATCTCCCCTCCAGATGCGGCCTCAGCTGCTCCACTCCGAACAATC   480

ACTGCTGACACTTTCCGCAAACTCTTCCGAGTCTACTCCAATTTCCTCCGGGGAAAGCTG   540

AAGCTGTACACAGGGGAGGCCTGCAGGACAGGGGACAGATGA                    583

Type: DNA
Length: 373
Sequence Name: TPL
Source: Adenovirus GI: 209811
                                                           SEQ ID NO. 4
CTTCCGCATCGCTGTCTGCGAGGGCCAGCTGTTGGGGTGAGTACTCCCTCTCAAAAGCGG    60

GCATGACTTCTGCGCTAAGATTGTCAGTTTCCAAAAACGAGGAGGATTTGATATTCACTG   120

GCCCGCGGTGATGCCTTTGAGGGTGGCCGCGTCCATCTGGTCAGAAAAGACAATCTTTTT   180

GTTGTCAAGCTTCCTTGATGATGTCATACTTATCCTGTCCCTTTTTTTTCCACAGCTCGC   240

GGTTGAGGACAAACTCTTCGCGGTCTTTCCAGTACTCTTGGATCGGAAACCCGTCGGCCT   300

CCGAACGGTACTCCGCCACCGAGGGACCTGAGCGAGTCCGCATCGACCGGATCGGAAAAC   360

CTCTCGAGGTACC                                                  373

Type: DNA
Length: 417
Sequence Name: VA I and VA II genes
Source: Adenovirus GI: 209811
                                                           SEQ ID NO. 5
```

```
                                         -continued
AGCGGGCACTCTTCCGTGGTCTGGTGGATAAATTCGCAAGGGTATCATGGCGGACGACCG    60

GGGTTCGAACCCCGGATCCGGCCGTCCGCCGTGATCCATGCGGTTACCGCCCGCGTGTCG   120

AACCCAGGTGTGCGACGTCAGACAACGGGGGAGCGCTCCTTTTGGCTTCCTTCCAGGCGC   180

GGCGGCTGCTGCGCTAGCTTTTTTGGCCACTGGCCGCGCGCGGCGTAAGCGGTTAGGCTG   240

GAAAGCGAAAGCATTAAGTGGCTCGCTCCCTGTAGCCGGAGGGTTATTTTCCAAGGGTTG   300

AGTCGCAGGACCCCCGGTTCGAGTCTCGGGCCGGCCGGACTGCGGCGAACGGGGGTTTGC   360

CTCCCCGTCATGCAAGACCCCGCTTGCAAATTCCTCCGGAAACAGGGACGAGCCCCT     417
```

The present invention utilizes a novel combination of five elements obtained from viruses and various other vector sources to develop a novel vector which gives a synergistic effect of these elements in the form of high expression of desired proteins in mammalian hosts cells. More specifically these expression vectors consist of a novel combination of the following five elements: a CMV immediate early promoter, an Adenovirus Tripartite Leader element (TPL) (GI: 209811), a hybrid (chimeric) Intron (SEQ. ID. No. 1), Adenoviral Virus Associated RNA genes I & II (GI: 209811), and a bovine growth hormone polyadenylation sequence.

When this novel combination of five elements is used in conjunction with additional elements in a basic vector that are necessary for its function as a vector, the novel vectors thus generated demonstrate synergistically higher expression than other vectors that comprise only some of these five elements in conjunction with the basic vector. Upon stable transfection our novel expression vector, also containing DHFR amplification marker, gave 80-100% higher expression of EPO than some of the best vectors reported in the literature.

More preferably, the novel expression vectors comprise a CMV immediate early promoter, an Adenovirus Tripartite Leader element (TPL) (SEQ ID No. 4), a hybrid (chimeric) Intron (SEQ. ID. No. 1), Adenoviral Virus Associated RNA genes I & II (SEQ ID No. 5), a cloning site, a mammalian cell selection marker, a prokaryotic cell selection marker, an amplification/selection marker, and a bovine growth hormone polyadenylation site, all present at suitable positions in the said vectors.

The proteins which can be produced using these vectors include, but are not limited to hormones like FSH, antibodies, chimeric proteins like etanercept, blood components like factor VII, growth factors like erythropoietin, cytokines like interferons, TNF and the like.

DESCRIPTION OF DRAWINGS

FIG. 1 is a schematic representation of various TNFR-IgGFc expression vectors including the novel expression vector pZRC-TNFR-IgGFc.

FIG. 2 depicts expression of TNFR-IgGFc protein from Cos-1 cells transiently transfected with various TNFR-IgGFc expression vectors including the novel expression vector pZRC-TNFR-IgGFc.

FIG. 3 is a schematic representation of various EPO expression vectors including the novel expression vector pZRC-EPO.

FIG. 4 depicts comparison of EPO expression in Cos-1 cells transiently transfected with the novel expression vector pZRC-EPO and another EPO encoding commercial expression vector pcDNA3.1.

FIG. 5 depicts the effect of increasing pressure of MTX on EPO expression from selected high producing clones of CHO-DHFR⁻ cells stably transfected with pZRC-EPO.

Source of Elements for the Construction of the Novel Expression Vector:

| | |
|---|---|
| Basic expression vector backbone | pcDNA3.1 (Invitrogen[1]) |
| Five regulatory elements - | |
| CMV promoter | pcDNA3.1 (Invitrogen) |
| Chimeric Intron | pIREShyg3 (Clontech[2]) |
| TPL | pCAV-NOT-TNFR (ATCC 68088) |
| VA I and II genes | pCAV-NOT-TNFR (ATCC 68088) |
| BGH polyadenylation sequence | pcDNA3.1 (Invitrogen) |
| DHFR minigene | pDHFR2.9 (ATCC 37165) |

[1]Product of Invitrogen Life Technologies, USA
[2]Product of Clontech Laboratories Inc., USA Abbreviations Used:

| | |
|---|---|
| CMV | Cytomegalovirus |
| TPL | Tripartite Leader |
| VA genes or VA I and II genes | Virus associated RNA genes I and II |
| BGH | Bovine growth hormone |
| EPO | Erythropoietin |
| TNFR-IgGFc | Fusion protein of tumor necrosis factor receptor and Fc portion of immunoglobulin G |

DESCRIPTION OF THE INVENTION

The present invention solves the problem of high cost of manufacturing described earlier in the background by providing novel expression vectors for the higher production of recombinant proteins in mammalian cells. These novel vectors utilize the previously well-known regulatory elements reported in prior art but comprise a unique combination of these elements that surprisingly produce synergistically higher expression. The present invention further provides a method of producing high levels of protein using these novel vectors.

The novel combination of elements utilized in this invention consists of:
a) a CMV immediate early promoter
b) a Adenovirus Tripartite Leader element (TPL) (Sequence ID No. 4 and GI: 209811)
c) a hybrid (chimeric) Intron (SEQ. ID. No. 1)
d) Adenoviral Virus Associated RNA genes I & II (Sequence ID No. 5 and GI: 209811), and
e) a bovine growth hormone polyadenylation site.

In order to develop these novel vectors the basic expression vectors that can be used for adding on the above described novel combination of elements comprise of:
a) a cloning site.
b) a suitable Mammalian cell selection marker selected from the group comprising of, but not limited to, drug resistant markers like neomycin, hygromycin, puromycin, and the like.

c) a suitable prokaryotic cell selection marker selected from the group comprising of, but not limited to, antibiotic resistance markers like ampicillin, kanamycin and the like.

d) an amplification/selection marker selected from the group comprising of, but not limited to dihydrofolate reductase, adenosine deaminase, ornithine decarboxylase, asparagine synthetase, glutamine synthetase, and the like.

The process of preparing the desired vector involves isolating the various elements of the vector from other vector sources or from their biological sources and inserting them into another vector that provides the backbone for the plasmid. The techniques used for these constructions are derived from those reported for vector construction in the prior art [Sambrook J et al., *Molecular Cloning—A laboratory Manual*, Cold Spring Harbor Laboratory Press, New York (1989)] with suitable modifications as may be necessary.

For the production of a desired protein, first the corresponding gene coding for the protein is obtained. The following techniques are generally employed, either alone or in combination, to obtain a desired gene:

(1) isolating messenger RNA (mRNA) for the desired gene and using this as a template for the production of complementary DNA (cDNA) by reverse transcription, (2) isolating the natural gene from genomic DNA libraries using a combination of appropriate gene-specific hybridization probes and restriction enzymes, (3) isolating the gene by specifically amplifying the specific gene fragment by polymerase chain reaction (PCR) using one or more pairs of gene specific primers, and (4) chemically synthesizing the gene from its component nucleotides.

The obtained gene is cloned in the cloning site of the novel vector by methods well known in the art. The resulting construct is transformed into a suitable mammalian host cell. The mammalian host cell which can be used for the process is selected from the group comprising of, but not limited to, CHO and CHO DHFR: cell lines, BHK1, NS0, COS cell lines and the like. The transformed cells are selected on the basis of their ability to grow in a suitable antibiotic containing media and then on their ability for expression of the desired protein. The selected clone is then grown under appropriate culture conditions for the growth and protein production to obtain high levels of the desired proteins. Gene copy number and the subsequent gene expression may be increased by selecting the high gene copy number cells under increasing selection pressure of a specific cytotoxic drug whose effect can only be nullified by increasing the copy number of the selection marker. Since gene amplification by cytotoxic selection pressure often converts a clone into a heterogenous population of cells with varying copies of the gene of interest, the final high producing clone is selected from heterogenous population by limiting dilution.

Example 1

Construction of TNFR-IgGFc Expression Vectors

A mammalian expression vector, pcDNA 3.1 (Invitrogen Life Technologies), was taken as a basic backbone vector to construct all our vectors. This vector consists of a CMV immediate early promoter and BGH polyadenylation signal sequence for the transcriptional control of the gene. These two elements form two of the five elements of our novel combination. This vector further consists of a multiple cloning site (MCS), a pUC origin of replication for bacteria, an ampicillin resistance gene for selection in *E. coli*, and a neomycin resistance gene for selection in mammalian cells. The remaining 3 elements of the novel combination of five elements namely, Adenoviral Tripartite leader sequence, a hybrid (Chimeric) intron consisting of 5' donor site of the adenovirus major late transcript and the 3' splice site of an mouse immunoglobulin, and the adenoviral VA RNA I & II genes were inserted into this pcDNA 3.1 backbone in various combinations in order to find a combination of elements that synergistically work together to give very high expression.

The cDNAs encoding the human INFR-IgGFc fusion gene (SEQ ID No 2) and human erythropoetin gene (SEQ ID No 3) were used as reporters to study the effect of the combination of these elements on protein expression. FIG. 1 depicts the expression vectors developed for TNFR-IgGFc and FIG. 3 depicts the same for EPO.

TNFR-IgGFc, is a fusion protein containing the 75 kDa TNFR (1-235 a.a.) and the Fc fragment of IgG1 (containing the CH2, CH3 and the hinge region) [U.S. Pat. No. 5,605, 690]. This fusion protein is sold as a drug named Enbrel (Amgen) for rheumatoid arthritis. It works by removing the inflammatory cytokine, TNF-α from the circulation. In order to clone TNFR I cDNA, Human placental total RNA (Clontech) was used as a template for reverse transcriptase-polymerase chain reaction (RT-PCR) based cloning of the desired sequence. Double stranded cDNA was synthesized from Human placental total RNA using MMLV reverse transcriptase (MBI Fermentas, USA) by gene specific priming [Maniatis et al., Molecular cloning; A Laboratory Manual (Cold Spring harbor Laboratory Press, Cold Spring Harbor, N.Y.), (1990)]. This cDNA was then subjected to 40 cycles of PCR amplification using 100 picomoles of gene specific degenerate oligonucleotide primers in a volume of 100 μl containing 50 mM Tris-Cl (pH8.3), 2.5 mM $MgCl_2$, 200 μM each of the 4 dNTPs and 2.5 units of Pfu Polymerase. Each PCR amplification cycle consisted of incubations at 94° C. for 30 sec (denaturation), 58° C. for 30 sec (annealing) and 72° C. for 1 min (extension). Amplified product of the PCR reaction was resolved on a 1% Agarose gel. The desired fragment of approx 705 base pairs in size was excised out from the gel and purified using Qiagen Gel extraction kit. This purified DNA fragment was ligated into the MCS of pcDNA 3.1 after restriction digestion of both the vector and the purified PCR product with EcoRI and PvuII (MBI Fermentas, USA). The ligation product was transformed in *E. coli* DH5α and transformants were scored on the basis of ampicillin resistance. Plasmid DNA isolated from about 20 such colonies was analysed for the presence of TNFR I cDNA by restriction digestion using various restriction enzymes. One such plasmid was sequenced using automated DNA sequencer (ABI) and found to be having the correct integration and sequence of the TNFR I cDNA in pcDNA 3.1 vector. This plasmid DNA was named pcDNA-TNFR.

Similarly, isolation of the IgG1Fc sequence was also done using human placental total RNA (Clonetech) as a template for RT-PCR based cloning. PCR was performed using a pair of gene specific oligonucleotide primers corresponding to the coding region of the IgG1Fc sequence (699 bp). Each PCR amplification cycle consisted of incubations at 94° C. for 30 sec (denaturation), 56° C. for 30 sec (annealing) and 72° C. for 1 min (extension). Amplified product of the PCR reaction was resolved on a 1% Agarose gel. The desired fragment of approx 725 base pairs in size was excised out from the gel and purified using Qiagen Gel extraction kit. This purified DNA fragment was ligated into pTZ57R (MBI Fermentas) vector after linearization of the vector and the digestion of purified PCR product using EcoRI and Not I (MBI Fermentas, USA). The ligation product was transformed in *E. coli* DH5α and transformants were scored on the basis of ampicillin resistance. Plasmid DNA isolated from about 10 such colonies was analysed for the presence of IgG1Fc cDNA by restriction digestion using various restriction enzymes. One such plasmid was sequenced using automated DNA sequencer (ABI) and found to be having the correct integration and sequence of the IgG1 Fc cDNA in the pTZ57R vector. This plasmid DNA was named pTZ57R-IgG1Fc.

pcDNA-TNFR-IgGFc

Fusion of TNFR I and IgG1Fc gene fragments was carried out by the following method. The cloned TNFR I fragment was isolated from pcDNA-TNFR by complete digestion with EcoRI and PvuII. IgG1Fc fragment was isolated from the pTZ57R-IgG1Fc construct by digesting it with Pvu II and Not I. These fragments were isolated from agarose gel using Qiagen gel extraction kit. Both these DNA fragments were mixed with the linearized vector pcDNA3.1 pre-digested with EcoRI and NotI, in a three piece ligation reaction. The ligation product was transformed in $E.$ $coli$ DH5α and transformants scored on the basis of ampicillin resistance. Plasmid DNA isolated from about 10 such colonies was analysed for the presence of TNFR-IgGFc fusion product by restriction digestion using various restriction enzymes. One such plasmid was sequenced using automated DNA sequencer (ABI) and found to be having the correct integration and sequence of the TNFR-IgGFc fusion product. This vector construct was named pcDNA-TNFR-IgGFc (FIG. 1) that contained the fusion gene flanked by the CMV promoter at the 5' end and the BGH polyadenylation sequence at the 3' end.

pcDNA-TPL-TNFR-IgG Fc-VA-DHFR

To develop this vector, first the Adenovirus TPL element was inserted downstream of the CMV promoter and upstream of the TNFR-IgG1Fc gene in pcDNA-TNFR-IgGFc. This was accomplished by digesting the pCAV/NOT-TNFR (ATCC 68088) with KpnI and Nde I in a complete digestion to take out the 700 bp fragment containing TPL, which was further purified using Qiagen Gel extraction kit. This 700 bp fragment was ligated in pcDNA-TNFR-IgGFc vector digested with KpnI and Nde I. The ligation product was transformed in $E.$ $coli$ DH5α and transformants were scored on the basis of ampicillin resistance. Plasmid DNA was analysed for the presence and orientation of the TPL in the resulting plasmid by restriction digestion using various restriction enzymes. One such positive plasmid DNA named pInt-TNFR-IgG-1 was then used for inserting two elements—one, the 1000 bp VA RNA gene, isolated from pCAV/NOT-TNFR by double digestion with EcoRI and Not I, and two, the DHFR minigene isolated from the plasmid pDHFR 2.9 (ATCC 37165) [Crouse G F et al, $Mol.$ $Cell.$ $Biol.,$ 3:257-266 (1983)] by complete digestion with BamHI & SspI. These two fragments, the DHFR minigene fragment & VA RNA gene fragment, were mixed with pint-TNFR-IgG-1 previously digested with MunI & BglII, in a three piece ligation reaction. The ligation product was transformed in $E.$ $coli$ DH5α and transformants were scored on the basis of ampicillin resistance. Plasmid DNA was analysed for the presence and orientation of the VA RNA gene and DHFR minigene in the resulting plasmid by restriction digestion using various restriction enzymes. This vector construct was named pcDNA-TPL-INFR-IgG1Fc-VA-DHFR (FIG. 1).

pcDNA-TPL-Intron-TNFR-IgGFc

The expression vector pcDNA-TPL-Intron-TNF'R-IgGFc was generated by inserting the chimeric intron downstream of Adenovirus TPL element and upstream of the TNFR-IgGFc gene in pInt-TNFR-IgG-1 vector. This was accomplished by digesting pIREShyg3 (Clontech) with BstXI and EcoRI in a complete digestion to take out the 350 bp chimeric intron fragment which was further purified using Qiagen Gel extrac-tion kit. This 350 bp fragment was ligated in the pInt-TNFR-IgG-1 vector construct previously digested with BstXI and EcoRI. The ligation product was transformed in $E.$ $coli$ DH5α and transformants were scored on the basis of Ampicillin resistance. Plasmid DNA was analyzed for the presence and orientation of the TPL, intron and TNFR1-IgG1Fc gene in the resulting plasmid by restriction digestion using various restriction enzymes. One such plasmid was sequenced using automated DNA sequencer (ABI) and found to be having the correct integration of the TPL, Chimeric intron and TNFR1-IgG1Fc gene in the vector. This vector construct was named pcDNA-TPL-Intron-TNFR-IgGFc (FIG. 1).

pcDNA-TPL-Intron-TNFR-IgGFc-VA-DHFR (pZRC-TNFR-IgGFc)

The above described plasmid DNA, pcDNA-TPL-Intron-TNFR-IgGFc was used for inserting two elements, the 1000 bp VA RNA gene isolated from pCAV/NOT-TNFR by a double digestion with EcoRI and Not I, and the DHFR minigene isolated from the plasmid pDHFR 2.9 by complete digestion with BamHI and SspI. The fragments for DHFR minigene and the VA RNA gene were ligated in pcDNA-TPL-Intron-TNFR-IgGFc previously digested with MunI & BglII, in a three piece ligation reaction. The ligation product was transformed in $E.$ $coli$ DH5α and transformants were scored on the basis of ampicillin resistance. Plasmid DNA was analyzed for the presence and orientation of the VA RNA gene and DHFR minigene in the resulting plasmid by restriction digestion using various restriction enzymes. Additionally, the integration was checked and confirmed by DNA sequencing. This vector construct was named pcDNA-TPL-Intron-TNFR-IgGFc-VA-DHFR, also called pZRC-TNFR-IgGFc (FIG. 1).

Example 2

Comparison of Expression Efficiencies of Various TNFR-IgGFc Expression Vectors by Transient Transfection For the transient transfection experiment, Cos 1 cells (ATCC No. CRL-1650), an African green monkey kidney fibroblast-like cells, were used. These cells were regularly maintained in the complete growth medium (Dulbecco's modified Eagle's medium with 4 mM L-glutamine and adjusted to contain 1.5 g/L sodium bicarbonate, 4.5 g/L glucose, 10% fetal bovine serum (FBS) and antibiotics) at a temperature of 37° C. and in an atmosphere of 5% carbon dioxide ($CO_2$). One day prior to transfection, cells growing in the mid-log phase were trypsinized and plated in duplicates in a 6-well plate at a density of 0.2 million cells/well in 3 ml complete growth medium and incubated at 37° C. and 5% $CO_2$. Transfection was carried out using Qiagen Polyfect reagent using previously known protocols. On the day of transfection, the transfection mix was prepared as follows. A total of 1.5 µg of DNA, dissolved in endotoxin free water was filtered using 0.2 µM syringe filter. For the largest construct, pZRC-TNFR-IgGFc, 1.5 µg vector was used as such, while for other smaller constructs an equimolar quantity (in terms of the TNFR-IgGFc gene) of the construct was mixed with empty vector to make up 1.5 µg total DNA. This DNA was first dissolved in cell growth medium, i.e. Dulbecco's modified Eagle's medium with 4 mM L-glutamine adjusted to contain 1.5 g/L sodium bicarbonate and 4.5 g/L glucose, containing no serum, or antibiotics to a total volume of 100 µl. Proper mixing was done by vortexing, and then a brief spin was given to this solution for a few seconds to remove the drops from the side walls and top of the tube. Then 10 µl of PolyFect Transfection reagent was added to this DNA solution. Proper mixing was done by pipetting the transfection mix up and down 5 to 7 times. The samples were then incubated at room temperature (20-25° C.) for 10 minutes to allow complex formation. While complex formation was taking place, the complete growth medium was gently aspirated from the 6 well plate. The seeded cells were washed with 3 ml of 1× sterile phosphate buffered saline (PBS). This was followed by addition of 1.5 ml fresh complete growth medium. After 10 minutes of complex formation, 0.6 ml of complete growth medium was added to the reaction tube containing the transfection complexes. The plates were then gently swirled to ensure proper mixing and incubated at 37° C., 5% $CO_2$. The spent media was removed from the wells after 40 and 64 hours of transfection and subjected to analysis of TNFR-IgGFc expression by ELISA as described below.

A required number of wells in a 96 well micro titer plate (Nunc Maxisorp) were coated with a volume of 100 μl/well of Goat anti-Human IgGFc Fragment antibody (Calbiochem, Cat no 401439) at a concentration of 2 μg/ml in PBS (pH 7.3). The plates were incubated at 4° C. overnight in humid conditions for efficient coating. After 12-18 hours, the unbound coating antibody was removed and the wells blocked with blocking buffer (1% BSA, 0.05% Tween 20, 5% skimmed milk prepared in 1×PBS, pH −7.2) and incubated for 1 hour at 37° C. After 1 hour of blocking the plates were washed thrice (250 μl each time) with PBST Buffer (1×PBS, 0.1% BSA, 0.05% Tween 20). Then 100 μl samples (unknowns and standards appropriately diluted in 1×PBS containing 1% BSA) were added to the wells in duplicates. For TNFR-IgGFc standard, an Enbrel (etanercept) multiple use vial containing 25 mg/ml Enbrel protein (manufactured by Immunex Corporation, US, marketed by Amgen and Wyeth Pharmaceuticals) was used. The concentrations of the standards used for generating the standard curve were 1 ng/ml, 2 ng/ml, 5 ng/ml, 10 ng/ml, 20 ng/ml, 40 ng/ml, and 80 ng/ml. After an incubation of 90 minutes, to allow antigen-antibody binding to take place, the plates were washed thrice (250 μl each time) with PBST Buffer and 100 μl detection antibody, Goat anti-Human IgGFc-HRP (Pierce, Cat No. 31416) diluted 1:20,000 in 1×PBS containing 1% BSA was added to the wells and incubated at 37° C. for 1 hr. The plates were washed thrice to remove unbound antibody-HRP conjugate. 100 μl of substrate solution containing 8 mg of OPD [o-Phenylenediamine (1,2-benzenediamine)dihydrochloride] powder (Sigma cat No P-1526) and 10 μl Hydrogen peroxide prepared in citrate-phosphate buffer (122.8 mg Citric Acid, anhydrous and 188 mg $Na_2HPO_4$ in 20 ml distilled Water and adjusted to pH 4.8 to 5.00) was added per well and incubated for 30 min in the dark at 37° C. The reaction was stopped by addition of 50 μl 1N sulphuric acid per well. Absorbance was measured in ELISA reader at 490 nm. Values for unknown samples were derived by SoftMax Pro (Molecular Devices) software using 4 Parameter fit standard curve based on the equation of Leveberg-Marquardt Method.

Results:

FIG. 2 depicts representative data from one such experiment. The highest expression was obtained with pZRC-TNFR-IgGFc (72.5±4.3 ng/ml), which was 21.97% higher than pcDNA-TPL-TNFR-IgGFc-VA-DHFR (59.44±1.8 ng/ml), 36.66% higher than pcDNA-TPL-Intron-TNFR-IgGFc (53.05±2.2 ng/ml) and 395.55% higher than pcDNA-TNFR-IgGFc (14.63±1.4 ng/ml). The synergistic effect of the five elements is further supported by the fact that the largest plasmid, pZRC-TNFR-IgGFc, which should show the poorest transfection efficiency was still giving the highest expression. The ability of the novel combination of elements of pZRC-TNFR-IgGFc to give high expression is further supported by other examples below.

Example 3

Construction of EPO Expression Vectors

Two EPO expression vectors were developed. The novel expression vector, pZRC-EPO, is similar to pZRC-TNFR-IgGFc the novel expression vector previously selected for its high expression via transient transfection experiments, and encodes the EPO gene instead of TNFR-IgGFc. The second vector is an EPO encoding commercial expression vector, pcDNA3.1, also carrying the gene for DHFR.

pcDNA-EPO-DHFR

In order to obtain human erythropoetin cDNA, total RNA derived from human kidney (Clontech) was used as a template for RT-PCR. Double stranded cDNA was synthesized from total RNA using MMLV reverse transcriptase (MBI Fermentas, USA) by gene specific priming [Maniatis et al., Molecular cloning; A Laboratory Manual (Cold Spring harbor Laboratory Press, Cold Spring Harbor, N.Y.), 1990]. The kidney cDNA was then subjected to 35 cycles of PCR amplification using 100 picomoles of gene specific degenerate oligonucleotide primers in a volume of 100 μl containing 50 mM Tris-Cl (pH8.3), 2.5 mM $MgCl_2$, 200 μM each dNTP and 2.5 units of Pfu Polymerase. Each PCR amplification cycle consisted of incubations at 94° C. for 30 sec (denaturation), 61° C. for 1 min (annealing) and 72° C. for 1 min (extension). Amplified product of the PCR reaction was resolved on a 1% agarose gel. The desired fragment of approx 590 base pairs was excised out of the gel and purified using Qiagen Gel extraction kit. This purified DNA fragment was ligated into the MCS of pcDNA 3.1 after restriction digestion of both the vector and the purified PCR product with EcoRI and XbaI (MBI Fermentas, USA) thereby generating sticky ends for directional cloning. The ligation product was transformed in E. coli DH5α and transformants were scored on the basis of ampicillin resistance. Plasmid DNA isolated from about 20 such colonies was analysed for the presence of EPO cDNA by restriction digestion using various restriction enzymes. One such plasmid was sequenced using automated DNA sequencer (ABI) and found to be having the correct integration and sequence of the EPO cDNA in the pcDNA 3.1 vector. This plasmid, pcDNA-EPO, was used for inserting the DHFR minigene which was isolated from pDHFR 2.9 by complete digestion with Hind III. The 2.9 Kb DHFR minigene was blunt ended using Klenow Polymerase (MBI Fermentas, USA) and ligated into pcDNA-EPO after linearizing it with Mlu I (MBI Fermentas, USA) and making it blunt ended using Klenow Polymerase (MBI Fermentas, USA). The ligation product was transformed in E. coli DH5α and transformants were scored on the basis of ampicillin resistance. Plasmid DNA, pcDNA-EPO-DHFR (FIG. 3) was analyzed for the presence and orientation of the DHFR minigene in the resulting plasmid by restriction digestion using various restriction enzymes.

pcDNA-TPL-Intron-EPO-VA-DHFR (pZRC-EPO)

This expression vector was generated by inserting the Adenovirus TPL downstream of the CMV promoter and upstream of the chimeric intron, which was further inserted upstream of EPO cDNA in pCDNA-EPO construct. Also the VA RNA gene and DHFR minigene were inserted in this vector between ampicillin resistance gene and the CMV promoter. This was accomplished by first digesting the pcDNA-TPL-Intron-TNFR-IgGFc vector with EcoRI and XbaI to remove the TNFR-IgGFc fragment. The 6 kb vector fragment thus generated was purified using Qiagen Gel extraction kit and ligated with the EPO gene having EcoRI and XbaI ends. The ligation product was transformed in E. coli DH5α and transformants were scored on the basis of Ampicillin resistance. Plasmid DNA was analyzed for the presence and orientation of the TPL, chimeric intron and EPO cDNA in the resulting plasmid by restriction digestion using various restriction enzymes. One such plasmid was sequenced using automated DNA sequencer (ABI) and found to be having the correct integration of the TPL, chimeric intron, and EPO gene in the vector. This plasmid DNA, named pint-EPO-1, was used for inserting the 1000 bp VA RNA gene, isolated from pCAV/NOT-TNFR by double digestion with EcoRI and Not I, and the DHFR minigene, isolated from the plasmid pDHFR 2.9 by complete digestion with BamHI & SspI. These two fragments were ligated with pInt-EPO-1 previously digested with MunI & Bgl II in a three piece ligation. The ligation product was transformed in E. coli DH5α and transformants were scored on the basis of ampicillin resistance. Plasmid DNA was analyzed for the presence and orientation of the VA RNA gene and the DHFR minigene in the resulting plasmid by restriction digestion using various restriction enzymes. Additionally, the integration was checked and confirmed by DNA sequencing. This vector construct was named pCDNA-TPL-Intron-EPO-VA-DHFR, also called, pZRC-EPO (FIG. 3).

Example 4

Comparison of Expression Efficiencies of Various EPO Expression Vectors by Transient Transfection For transient transfection Cos 1 cells were grown and handled as described above. All transfections mixtures were also made as described in the previous example. The transfection procedures were also followed as described in the example above and spent media was removed from the cells after 40 hrs and 64 Hrs of transfection and subjected to ELISA for analysis of EPO expression as described below.

First, 96 well micro titer plates (Nunc Maxisorp) were coated with 50 μl/well volume of a mouse monoclonal antibody against recombinant human EPO(R&D Systems Anti-hEPO Purified Mouse Mab, Clone 9C21D11, Cat# MAB287) at a concentration of 2 μg/ml in carbonate buffer, pH-9.6. These plates were incubated at 4° C. overnight in humid conditions for efficient coating. After 12-18 hours the coating antibody was removed and wells were blocked with a blocking buffer as described above. After 1 hour of blocking the plates were washed thrice (250 μl each time) with PBST Buffer. Then 50 μl samples diluted appropriately in 1×PBS containing 1% BSA were added to the wells in duplicates. For EPO standard, Eprex 4000 (recombinant human EPO 4000 IU/0.4 ml) manufactured by Cilag AG Schaffhausen Switzerland, was used. The concentrations of standards used for generating the standard curve were: 4 IU/ml, 2 IU/ml, 1 IU/ml, 0.4 IU/ml, 0.2 IU/ml, and 0.1 IU/ml. After an incubation of 90 minutes to allow antigen-antibody binding, the plates were washed thrice (250 μl each time) with PBST buffer. This was followed by the addition of 50 μl volume of primary antibody (rabbit anti-human EPO, purified IgG, R&D Systems, Cat # AB-286-NA) at a concentration of 2 μg/ml in 1×PBS containing 1% BSA further followed by incubation for 1 hour at 37° C. After 1 hour incubation, the plates were washed thrice (250 μl each time) with PBST buffer and 50 μl detection antibody/secondary antibody (goat anti-rabbit IgG-HRP, Bangalore Genei, Cat # HPO020) diluted 1:8000 in 1×PBS containing 1% BSA, pH-7:2, was added followed by incubation for 1 hour at 37° C. The plates were washed thrice (250 ul each time) with PBST Buffer to remove unbound conjugate. This was followed by substrate addition. For this 100 μl of substrate solution (prepared as described earlier) was added per well and incubated for 30 min in the dark at 37° C. The reaction was stopped by addition of 50 μl 1N sulphuric acid per well. Absorbance was measured in ELISA reader at λ490 nm. Values for unknown samples were derived by SoftMax Pro (Molecular Devices) using 4 Parameter fit standard curve based on the equation of Leveberg-Marquardt Method.

Results:

FIG. 4 depicts representative data from one such experiment. The highest expression was obtained with pZRC-EPO (276.53±3.09 ng/ml), which was 984.85% higher than pcDNA-EPO-DHFR (25.49±2.38 ng/ml). This data supports the finding of Example 3, that the novel expression vector containing a novel combination of five elements gives very high expression for different reporter genes.

The superior ability of the novel combination of elements in pZRC-EPO was confirmed in stably transfected cells also as can be seen in Example 7 below.

Example 5

Stable Transfection of CHO DHFR⁻ Cells with pZRC-EPO

CHO DHFR⁻ cells (chinese hamster ovary cells mutant for gene encoding for dihydrofolate reductase) were regularly maintained in complete medium (MEM α medium (Sigma) supplemented with 10% FBS (Hyclone) and a mixture of hypoxanthine and thymidine). At the time of transfection cells growing in mid log phase were trypsinized from a T25 cm$^2$ flask, washed once in 5 ml complete medium, and resuspended in PBS. Fifteen micrograms of pZRC-Epo linearized with SspI restriction enzyme was added to 1×10$^6$ cells and electroporated (350 V) using a Stratagene Eectroporator 1000. After a brief recovery period of 48 h in complete medium, the cells were subjected to double selection by maintaining them in selection medium (10% dialyzed FBS supplemented MEM α medium, without the addition of a mixture of hypoxanthine and thymidine, plus 500 μg/ml G418 (Sigma)). The cells were returned to the 5% $CO_2$, 37° C. incubator and were allowed to grow for a period of two weeks. Medium change was given every 3 days. Patches of stable transfectants started developing after 12 days of the selection process. On the 15$^{th}$ day of selection, cells were trypsinized. To isolate single cell clones from this mixed population of stable transfectants, cells were diluted using limiting dilution technique in 96 well plates. Wells found to contain single cells under the microscope were marked and regular medium change was given to these single cell clones. After about 12-14 days, these wells were found to be 70-80% confluent. The cells were transferred to 24 well plates and grown for 48-72 hrs before transfer to 6 well plates. These single cell clones were seeded in 6 well plates at a density of 0.1×10$^6$ cells per well in the selection media. Spent media was removed from these wells after 48 hrs and the cells were counted. This spent media was analysed for EPO expression by ELISA as described above. The results were expressed as total amount of EPO protein secreted/10$^6$ cells/48 hrs.

Ten high expressing clones were selected and subjected to methotrexate (MTX)-based, gene amplification process starting by adding 25 nM MTX to the selection media. Fresh medium was replenished after every 3 days. The cells were grown in one concentration of MTX for about 20-25 days till they got adapted. After every stage of increasing concentration of MTX, the cells were analyzed for expression levels at 6 well plate level as described earlier. One of these selected 10 clones did not survive at 25 nM MTX. All other nine clones were subjected to continuously increasing MTX concentrations of 100 nM, 400 nM and finally, 2 µM MTX. FIG. 5 shows expression of these heterogenous populations derived from MTX amplification of clonal populations at the end of various stages of MTX amplification.

Selection with MTX converts a clonal population of cells into a heterogenous population. Therefore, in order to isolate high expressing single cell clones from these MTX-amplified heterogenous populations, first one heterogenous population, 41H9, was selected at 400 nM MTX stage. These cells were setup for clone selection by limiting dilution as described above. After about 14-16 days, the wells of 96 well plates were found to be 70-80% confluent. The cells were transferred to 24 well plates and grown for 48-72 hrs before transfer to 6 well plates. These single cell clones were seeded in 6 well plates at a density of $0.1 \times 10^6$ cells per well in the selection media containing 400 nM MTX. Spent media was removed from these wells after 48 hrs and the cells were counted. The spent media was taken for expression analysis by ELISA as described above. The results were expressed as total amount of EPO protein secreted/$10^6$ cells/48 hrs. Table 1 shows expression of these single cell clones which were originally derived from the 41H9 heterogenous population. High expressing clones were expanded and frozen down as master cell banks for commercial production of EPO.

TABLE 1

| Clone | Protein yield in µg/million cells/48 h |
|---|---|
| 41H9.3G10 | 9.64 |
| 41H9.4G10 | 13.97 |
| 41H9.4H9 | 14.18 |
| 41H9.5G9 | 12.61 |
| 41H9.10H12 | 11.91 |
| 41H9.1E8 | 10.93 |
| 41H9.2F9 | 12.32 |
| 41H9.5E10 | 12.24 |
| 41H9.8C9 | 12.68 |
| 41H9.10B10 | 13.56 |
| 41H9.2G8 | 6.15 |
| 41H9.4F9 | 7.31 |
| 41H9.1C8 | 14.92 |
| 41H9.7H9 | 5.85 |

Example 6

Production of EPO from Stable Expression Clones in Flasks

Two heterogenous populations of cells from those depicted in FIG. 5, namely 56D12 and 41H9, that were being selected at 100 nM MTX and 400 nM MTX respectively, were tested for protein production in T75 flask level. 175 cm² flasks were inoculated with 2.1 million cells in hypoxanthine- and thymidine-free, MEMα medium, supplemented with 10% dialyzed FBS (JRH Biosciences), and 600 µg/ml G418 along with appropriate concentration of MTX for the respective heterogenous population. Flasks were returned to $CO_2$ incubators at 37° C., 5% $CO_2$ for 72 Hours. Cell monolayer was found to be about 80-85% confluent after 72 hours of incubation. At this point, the old spent media was removed and cell monolayer was washed with Dulbecco's PBS. To the washed monolayers, 15 ml of production medium [IMDM: Ham's F12 (1:1) supplemented with 10 mg/L rh-insulin, 2 mM glutamine, amino acid mixture, 0.2 mM, N-Acetyl cystine, 0.25% lactalbumin, 2 mg/L $FeSO_4$, 25 mg/L dextran sulfate, 0.05% pluoronic acid, 5 mg/L Hydrocortisone, and 1 mM Na-butyrate] was added. The cells were incubated in $CO_2$ incubator at 33° C. for a period of four days. After four days the spent media was removed aseptically and analysed by ELISA. Table 2 shows expression of these two clones in production media at the T75 flask level.

TABLE 2

| Name of heterogenous population | Protein yield in mg/l after four days |
|---|---|
| 56D12 (100 nM MTX) | 21 mg/l |
| 41H9 (400 nM MTX) | 43 mg/l |

Example 7

High Level Production Of EPO in Roller Bottles

One of the representative heterogenous populations described above, 41H9, that was already adapted to 2 µM MTX, was used for a roller bottle study to analyze the protein production at larger scales. The 41H9 cells were expanded using T75 and T175 culture flasks so as to get enough number of cells for seeding roller bottles.

5 roller bottles were inoculated with 30 million cells each in a 2 µM MTX-supplemented, hypoxanthine- and thymidine-free, MEMα medium (Sigma), containing 10% dialyzed FBS (JRH Biosciences), and 600 µg/ml G418. After mixing the cells in the medium the roller bottles were returned to the roller bottle incubator at 37° C. and a roller speed of approx. 0.35 rpm for growth. The cells were observed after 24 Hrs and found to be growing well. Again the bottles were returned to incubator for growth and observed under the microscope every 24 hrs. After 96 hours of inoculation, cell monolayers were about 80-85% confluent. At this point, the old spent media was removed and 210 ml/bottle production medium [IMDM:Ham's F12 (1:1) supplemented with 10 mg/L rh-insulin, 2 mM glutamine, amino acid mix, 0.2 mM N-Acetyl cystine, 0.25% lactalbumin, 2 mg/L $FeSO_4$, 25 mg/L dextran sulfate, 0.05% pluoronic acid, 5 mg/L hydrocortisone, and 1 mM Na-butyrate] was added to each of the bottles. The cells were incubated in roller bottle incubators for a period of seven days. After this period the spent media was removed aseptically from the roller bottles, analysed by ELISA as described previously, and depicted in Table 3.

TABLE 3

| Name of heterogenous population | Protein yield in mg/l after seven days |
|---|---|
| 41H9 (2 µM MTX) | 91 mg/L |

This level of productivity from a heterogenous, stably transfected and MTX-amplified, population from which individual clones have not yet been selected shows an expression level which is much better than that reported in the literature for individual stable clones. For example, stable clones generated by transfection and gene amplification up to 20 nM MTX using a vector containing SR α promoter, AMV RNA 4 leader sequence, DHFR and Zeocin resistance could give a clone of 45 IU/ml (equivalent to 0.346 µg/ml) [Jang H P et al, *Biotechnol. Appl. Biochem,* 32:167-172, (2000)].

U.S. Pat. No. 5,955,422 reports that clones generated from CHO DHFR-cells co-transfected with a vector containing a genomic copy of EPO gene under the control of SV40 promoter and poly A sequence and a vector containing DHFR, upon MTX gene amplification gave a yield of 750 to 1470 U/million cells/48 Hrs (or 375 to 735 U/million cells/24 Hrs)

in serum free production media in roller bottles. Another U.S. Pat. No. 5,888,774, reports an EPO clone generated from CHO-K1 cells transfected with a vector containing EPO cDNA driven by EF1 promoter with apoB SAR elements and neomycin resistance that could produce 1500 to 1700 IU of EPO/million cells/24 Hrs (analysed between day 3 and day 4 of culture). In contrast, a seven day representative media sample of our heterogenous population, 41H9, previously adapted to 2 µM MTX was found to contain 11830 IU/ml in a roller bottle as judged by ELISA. Based on the estimated cell densities of $10^8$ to $1.5 \times 10^8$ cells per roller bottle, the rate of production of EPO in the 7-day, 210 ml culture was 2366 to 3549 IU/$10^6$ cells/24 Hrs, significantly higher than the levels described above for other reported vectors utilizing various other combinations of regulatory elements.

Similarly, Sung Kwan Yoon et al [*Biotechnology and Bioengineering*, 82(3):289-298, (2003)] reported a fully optimized process for production of EPO using a cell line developed in CHO DHFR-cells by gene amplification process up to 5 µM MTX selection pressure gave a yield of approximately 50 µg/ml after a culture period of about 200 hrs at 33° C. Our pZRC-EPO stably transfected, heterogenous population 41H9 which was adapted to a comparatively lower level of MTX (2 µM) was able to produce 11,830 IU/ml (91 µg/ml) in a 168 hrs culture as judged by ELISA.

These levels of expression of EPO with the novel expression vector, pZRC-EPO, are 81-100% higher than those reported for the best vectors in the literature. The method of EPO production described above for heterogenous population, 41H9, can also be applied to stable clones reported in Example 5, Table 1.

The novel vector of the present invention has been deposited with IMTECH, Chandigarh, India a recognized depository under the Budapest treaty. The accession number is awaited.

We claim:

1. A mammalian expression vector comprising:
   (i) a CMV promoter;
   (ii) an intron consisting of the nucleic acid sequence of SEQ ID NO: 1,
   (iii) a tripartite leader (TPL);
   (iv) a virus associated (VA) gene;
   (v) a bovine growth hormone (BGH) polyadenylation sequence; and
   (vi) a nucleic acid sequence encoding a protein of interest.

2. The vector of claim 1, wherein the TPL consists of the nucleic acid sequence of SEQ ID NO: 4.

3. The vector of claim 1, wherein the VA gene consists of the nucleic acid sequence of SEQ ID NO: 5.

4. The vector of claim 1, further comprising a selection marker selected from the group consisting of dihydrofolate reductase, adenosine deaminase, ornithine decarboxylase, asparagine synthetase, and glutamine synthetase.

5. The vector of claim 1, wherein the protein is recombinant erythropoietin.

6. The vector of claim 1, wherein the protein is TNFR-IgGFc.

7. The vector of claim 1, wherein the protein is rituximab, trastuzumab, bevacuzumab or other monoclonal antibody.

8. An isolated mammalian cell comprising the vector of claim 1.

9. The isolated mammalian cell of claim 8, wherein the cell is selected from the group consisting of a Cos, CHO, CHO DHFR−, BHK1, and NS0 cell.

10. A mammalian expression vector comprising:
    (i) a CMV promoter;
    (ii) an intron consisting of the nucleic acid sequence of SEQ ID NO: 1,
    (iii) a tripartite leader (TPL) consisting of the nucleic acid sequence of SEQ ID NO: 4;
    (iv) a virus associated (VA) gene consisting of the nucleic acid sequence of SEQ ID NO: 5;
    (v) a bovine growth hormone (BGH) polyadenylation sequence; and
    (vi) a nucleic acid sequence encoding a protein of interest.

11. The vector of claim 10, wherein the protein is recombinant erythropoietin.

12. The vector of claim 10, wherein the protein is TNFR-IgGFc.

13. An isolated mammalian cell comprising the vector of claim 10.

14. The vector of claim 10, further comprising a selection marker selected from the group consisting of dihydrofolate reductase, adenosine deaminase, ornithine decarboxylase, asparagine synthetase, and glutamine synthetase.

15. A method for expressing a protein in CHO cells comprising:
    (a) constructing a vector comprising:
        (i) a CMV promoter;
        (ii) an intron consisting of the nucleic acid sequence of SEQ ID NO: 1,
        (iii) a tripartite leader (TPL);
        (iv) a virus associated (VA) gene;
        (v) a bovine growth hormone (BGH) polyadenylation sequence; and
        (vi) a nucleic acid sequence encoding a protein of interest; and
    (b) transfecting CHO cells with the vector such that the protein is expressed.

16. The method of claim 15, wherein the protein is recombinant erythropoietin.

17. The method of claim 15, wherein the protein is TNFR-IgGFc.

18. The method of claim 15, wherein the protein is rituximab, trastuzumab, bevacuzumab or other monoclonal antibody.

19. The method of claim 15, wherein the protein is selected from the group consisting of TN FR-IgGFc, rituximab, trastuzumab, bevacuzumab or other monoclonal antibody.

* * * * *